United States Patent
Rønvig et al.

(10) Patent No.: US 6,926,525 B1
(45) Date of Patent: Aug. 9, 2005

(54) INSTRUMENT FOR THE PARALLEL INSTALLATION OF DENTAL IMPLANTS

(75) Inventors: Jørn Rønvig, Violvej 1, DK-8722 Hedensted (DK); Henning Lehmann Bastian, Odense (DK)

(73) Assignees: Jørn Rønvig, Hedensted (DK); Tandlaegeselskabet V/ Henning Lehmann Bastian, Odense (DK)

( * ) Notice: Subject to any disclaimer, the term of this patent is extended or adjusted under 35 U.S.C. 154(b) by 196 days.

(21) Appl. No.: 10/129,836

(22) PCT Filed: Nov. 9, 2000

(86) PCT No.: PCT/DK00/00622

§ 371 (c)(1),
(2), (4) Date: Jul. 3, 2002

(87) PCT Pub. No.: WO01/34055

PCT Pub. Date: May 17, 2001

Related U.S. Application Data (60) Provisional application No. 60/184,071, filed on Feb. 22, 2000.

(30) Foreign Application Priority Data

Nov. 10, 1999 (DK) ............................... 1999 01620
Feb. 2, 2000 (DK) ............................... 2000 00175

(51) Int. Cl.$^7$ ............................................. A61C 3/02
(52) U.S. Cl. ....................................................... 433/76
(58) Field of Search ....................... 433/75, 76; 606/96

(56) References Cited

U.S. PATENT DOCUMENTS 1,321,130 A * 11/1919 Schlueter (Continued)

FOREIGN PATENT DOCUMENTS

DE 37 30 055 A 3/1989

(Continued)

OTHER PUBLICATIONS

Leonard L. Portnoy, A Non-Parallel Implant Overdenture, CDA Journal, Aug. 1995, pp. 73-76.

(Continued)

*Primary Examiner*—Cary E. O'Connor
(74) *Attorney, Agent, or Firm*—Birch Stewart Kolasch & Birch, LLP (57) ABSTRACT

The present invention relates to a dental device and a dental system that functions to assist in placing implants at a predetermined angle, in particular in inserting implants parallel with each other or parallel with a non-implant appliance supported in the mouth, and to a method of installing implants in parallelism. The present invention relates to an apparatus for parallel insertion of dental implants comprising a paralleling apparatus and a dental handpiece, wherein the paralleling apparatus comprises at least a first arm and a second arm, said first arm comprising means for pivotably connecting an anchor member thereby defining a first axis of rotation, said second arm comprising means for pivotably connecting attachment means of a dental handpiece thereby defining a second axis of rotation, said arms being pivotably connected by hinging means defining a least a third axis of rotation, said first and second axes of rotation being substantially parallel, wherein the dental handpiece further comprises means for securing a burr, the attachment means and the burr securing means being so arranged that when the dental handpiece is pivotably connected to the second arm, the drilling axis of the burr is at a distance to the second arm and at a direction substantially parallel to the second axis of rotation, and wherein the second arm and/or the attachment means of the dental handpiece comprises means for determining the level of position of the handpiece in relation to the second arm.

33 Claims, 3 Drawing Sheets

U.S. PATENT DOCUMENTS

| | | | |
|---|---|---|---|
| 2,299,151 A * | 10/1942 | Kestler | |
| 2,675,615 A | 4/1954 | Rosenberg | |
| 3,063,149 A | 11/1962 | Suga | |
| 3,380,163 A * | 4/1968 | Westerman | |
| 4,344,755 A * | 8/1982 | Gold et al. | 433/76 |
| 5,133,660 A | 7/1992 | Fenick | 433/76 |
| 5,183,414 A | 2/1993 | Czerniawski | 433/76 |
| 5,302,122 A | 4/1994 | Milne | 433/76 |
| 5,316,477 A | 5/1994 | Calderon | 433/173 |
| 5,320,529 A | 6/1994 | Pompa | 433/76 |
| 5,484,285 A | 1/1996 | Morgan et al. | 433/173 |
| 5,531,596 A * | 7/1996 | Melde | 433/104 |
| 5,531,751 A | 7/1996 | Schultheiss et al. | 406/96 |
| 5,556,278 A | 9/1996 | Meitner | 433/76 |
| 5,613,852 A | 3/1997 | Bavitz | 433/173 |
| 5,636,986 A | 6/1997 | Pezeshkian | 433/76 |
| 5,741,133 A | 4/1998 | Gordils et al. | 433/76 |
| 5,888,065 A | 3/1999 | Sussman | 433/76 |
| 5,915,962 A | 6/1999 | Rosenlicht | 433/76 |
| 5,967,777 A | 10/1999 | Klein et al. | 433/95 |
| 5,989,024 A * | 11/1999 | Jonjic | 433/76 |

FOREIGN PATENT DOCUMENTS

| | | |
|---|---|---|
| DE | 37 30 055 A1 | 3/1989 |
| DE | 296 08 550 U | 7/1996 |
| DE | 296 08 550 U1 | 8/1996 |
| DE | 196 05 394 A | 10/1996 |
| DE | 196 05 394 A1 | 10/1996 |
| EP | 0 930 050 A1 | 7/1999 |
| WO | 94/00073 A1 | 1/1994 |
| WO | WO 97/49351 A1 | 12/1997 |

OTHER PUBLICATIONS

Weingart et al., Treatment of fully edentulous patients with ITI implants, Clinical Oral Implants Research, 2000, 11 (Suppl.), pp. 69-81.

Mericske-Stern et al., Management of the edentulous patient, Clinical Oral Implants Research, 2000, 11 (Suppl.), pp. 108-124.

Lechner et al., Prosthodontic procedures for implant reconstruction, 1. Diagnostic procedures, Australian Dental Journal, 1992, 37(5), pp. 353-359.

Amerian D. Sones, Complications with osseointegrated implants, The Journal of Prosthetic Dentistry, 1989, vol. 62, No. 5, pp. 581-585.

Engelman et al., Optimum placement of osseointegrated implants, The Journal of Prosthetic Dentistry, 1988, vol. 59, No. 4, pp. 467-473.

Golden et al., Fabrication of a two-piece superstructure for a fixed detachable implant-supported mandibular complete denture, The Journal of Prosthetic Dentistry, 2000, vol. 84, No. 2, pp. 205-209.

Bruggenkate et al., Symmetrical Placement of Implants in the Edentulous Mandible: A New Technique, J. of Oral Maxillofac. Surg., 1990, vol. 48, pp. 1124-1126.

Bruggenkate et al., Parallelism of Hollow-Cylinder ITI Implants: An Experimental Study, The International Journal of Oral & Maxillofacial Implants, 1989, vol. 4, No. 4, pp. 293-296.

Shepherd et al., A General Dentist's Guide to Proper Dental Implant Placement from an Oral Surgeion's Perspective, Compedium, 1996, vol. 17, No. 2, pp. 118-122.

Sethi et al., Predicting Esthetics in Implant Dentistry Using Multiplanar Angulation: A Technical Note, The International Journal of Oral and Maxillofacial Implants, 1995, vol. 10, No. 4, pp. 285-490.

Clelland et al., A Three-Dimensional Finite Element Stress Analysis of Angled Abutments for an Implant Placed in the Anterior Maxilla, Journal of Prosthodontics, 1995, vol. 4, No. 2 (Jun.), pp. 95-100.

Irwin A. Small, The fixed mandibular implant: its use in reconstructive prosthetics, JADA, 1990, vol. 121, Sep., pp. 369-374.

Freesmeyer et al., Implantatgetragener Zahnersatz, Z Zahnarztl Implantol, 1989, pp. 124-130.

* cited by examiner

INSTRUMENT FOR THE PARALLEL INSTALLATION OF DENTAL IMPLANTS

This application is the national phase under 35 U.S.C. § 371 of PCT International Application No. PCT/DK00/00622 which has an International filing date of Nov. 9, 2000, which designated the United States of America.

The present invention relates to a dental device and a dental system that functions to assist in inserting implants in the jaw in particular in placing implants parallel with each other or parallel with a non-implant appliance supported in the mouth, and to a method of installing implants in parallelism.

BACKGROUND

Implants are now commonly used for providing anchor points in the jaw to which supports are made for a single tooth, for multiple teeth, for bridges and/or for prosthetic devices. If more than one implant is to be installed in the jaw or if implants are to be used in combination with existing non-implant appliances, it is highly desirable that all the implants be parallel with each other. This parallelism makes for precise and uniform angulation of implants in the jaw and also provides precise abutments in anchor teeth for bridges and the like.

Several attempts in have been made in the prior art for obtaining a paralleling device. For example a device consisting of two arms, wherein one arm is attachable to an anchor means whereas the other arm is used to guide the burr for drilling the necessary holes. The burr is typically led through a bore in the other arm. It is however difficult to obtain a precise parallel alignment with the anchor means when the burr is led through a bore in the arm since some tolerance is necessary for the burr to be able to perform the relevant drilling action. Furthermore, the device requires that only burrs of a certain diameter are acceptable, namely those fitting into the bore of the arm.

U.S. Pat. No. 5,302,122 discloses a dentistry implant paralleling device consisting of several identical shaped links capable of being pivotably connected for forming a chain. Furthermore, one of the links may be connected to a dentist handpiece and a link at the other end of the chain may be attached to an anchor means in the jaw. By the use it is possible to drill a hole in the jaw parallel to the anchor means. It is however not possible to correct for the different height levels in the jawbone when drilling. Furthermore, due to the several links necessary to provide the relevant movements some uncertainty with respect to the parallelism of the holes remains, since it is not possible to design the releasable links without marginal tolerances. This is also the case in DE 37 30 055 describing an instrument for parallelly directing a dentist's burr. The instrument consists of three links, connected so that the links cannot be vertically moved in relation to each other during use of the instrument, and in DE 19 60 394 describing an instrument for parallelly directing a dentist's burr. The instrument consists of two telescopic arms connected through a cardan joint. In another reference, U.S. Pat. No. 5,741,133, an instrument for parallelly drilling holes for dental implants, wherein the instrument has one arm, is described. This provides a better stability, but does also lead to an undesirably low mobility of the instrument in use.

SUMMARY OF THE INVENTION

The present invention relates to an apparatus for insertion of dental implants in a predetermined angle with respect to another implant, existing teeth or the like. In particular the invention relates to an apparatus for parallel insertion of dental implants comprising a paralleling apparatus and a dental handpiece.

The invention will be described by reference to parallel insertion.

In another embodiment the present invention relates to a system for parallel insertion of dental implants comprising a paralleling device and a dental hand piece, wherein the paralleling device comprises at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said arms being pivotably connected by hinging means defining a least a third axis of rotation, said first and second axes of rotation being substantially parallel, wherein the dental handpiece further comprises means for securing a burr, the attachment means and the burr securing means being so arranged that when the dental handpiece is pivotably connected to the second arm, the drilling axis of the burr is at a distance to the second arm and at a direction substantially parallel to the second axis of rotation, and wherein the second arm and/or the attachment means of the dental handpiece comprises means for determining the level of position of the handpiece in relation to the second arm.

In another embodiment the present invention relates to a system for parallel insertion of dental implants comprising a paralleling device and a dental handpiece, wherein the paralleling device comprises at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said arms being pivotably connected by hinging means defining a least a third axis of rotation, said first and second axes of rotation being substantially parallel, wherein the dental handpiece further comprises means for securing a burr, the attachment means and the burr securing means being so arranged that when the dental handpiece is pivotably connected to the second arm, the drilling axis of the burr is at a distance to the second arm and at a direction substantially parallel to the second axis of rotation, and wherein the first arm and/or the anchor member comprises means for determining the level of position of the first arm in relation to the anchor member.

In a further embodiment the present invention relates to an apparatus or paralleling device for parallel insertion of dental implants, said apparatus comprising:

at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, said first, second and third axes of rotation being substantially parallel, wherein, for both the first and the second arms, the proximal end of an arm has a contact surface with the width of said contact surface being larger than the height or thickness of the proximal end of the corresponding arm, said hinging means comprising an axle or shaft connecting the proximal ends with the two contact surfaces laying flat up to each other in a supportive way.

In yet another embodiment the present invention relates to an apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said arms being pivotably connected by hinging means defining a least a third axis of rotation, said first and second axes of rotation being substantially parallel, wherein the hinging means and/or at least one arm comprise fixation means for locking two pivotably connected arms at a fixed angle.

When the instrument is adapted for being used for insertion in angles different from parallellity, at least one of the arms comprises means for receiving attachment means and/or anchor member at another angle than parallel with the third axis of rotation.

By use of the present invention it is possible to drill holes for providing parallel anchor points in the jaw while at the same time securing that the system may adjust for the various height levels in the jaw. In the present context the term "non-releasably, pivotably connected" is intended to mean that at least during the drilling performance the proximal ends of the two arms are secured in the same plane, preferably the horizontal plane and cannot be disengaged.

Because the drilling axis does not pass any of the arms, the system may be used in connection with burrs of a wide variety of diameters.

A further object of the invention is a method for parallel insertion of a dental implant in a jaw bone comprising
establishing a first hole in the jaw bone,
arranging an anchor means in the hole,
using said anchor means as a pivot guide for an arm of a system as defined above,
guiding a handpiece attached to the system said handpiece comprising a burr for drilling second hole(s) in the jaw bone that are parallel with the first hole, and
inserting the implant.

DRAWINGS

FIGS. 4a and 4b shows a bush with a stopper mechanism and a bush without stopper mechanism, respectively.

DETAILED DESCRIPTION OF THE INVENTION

The invention is described in detail in relation to parallel insertion apparatus.

When inserting implants in the jaw of an individual it is of importance to secure that the holes drilled in the jaw are parallel in order to provide parallel anchor points for the implants. Furthermore, it is of importance that it is possible to adjust for the various height levels in the jaw of the individual when drilling the holes. The present invention describes the solution to these problems which is described in relation to the system and the individual parts of the system for parallel insertion of dental implants is described in greater details, as well as the method for using the system.

A major part of the system is a paralleling apparatus comprising at least two arms, a first arm and a second arm pivotably connected through a hinging means whereby the arms may rotate in relation to each other. The first arm and the second arm are preferably of an elongated form having increased width in the proximal end for forming the hinging means. The two arms have substantially identical dimensions. The arms may appear as straight arms or may be curved. Furthermore, the arms may be provided with one or more recesses for allowing the burr an increased radius of action and/or for decreasing the weight of the apparatus.

In a preferred embodiment the proximal end of each arm is formed as an essential circular extension of the arm provided with a bore through which a pin of the hinging means may be inserted.

The first arm comprises means for pivotably connecting said arm to an anchor member which anchor member is secured in the jaw of the individual to be treated. Thereby the anchor means serves as a pivot guide for the first arm. In a preferred embodiment the means for pivotably connecting the anchor means is a bore in the distal end of the first arm. More preferred the means is a bore through the arm, said bore being dimensioned to receive the anchor means without leaving any tolerances that would otherwise disturb the ability of securing parallel holes.

The anchor means of the jaw may be any suitable means normally used when inserting implants, such as a first burr also called the pilot burr, said first burr being used solely for drilling a pilot hole in the jaw bone. The pilot hole is used for securing the parallelism of all the other holes to be used for the implants. In another embodiment the anchor means is an anchor pin inserted into the pilot hole. The dimensions of a pilot burr are often from 2 to 3 mm in diameter, mostly about 2.35 mm.

The anchor means may also be a hinge or a cap on one or more teeth, whereby it is possible to obtain parallellity with existing teeth.

In order to adjust for the various height levels in the jawbone, a bush is preferably incorporated in the bore of the distal end of the first arm for receiving the anchor member. The bush is preferably comprising a stopping mechanism whereby the anchor means may be received in the bush until a certain stop. Thereby the paralleling apparatus may be height adjusted in relation to the anchor means, by using bushes having a stopping mechanism in different heights. Preferably a sleeve is arranged on the bush for determining the positioning level of the first arm in relation to the anchor member.

Alternatively, a set of anchor members may also be adapted for varying the height level of the first arm in relation to the jawbone. Thus, in a preferred embodiment an anchor member comprises a shaft having a lower portion being insertable into a hole or bore in the jaw bone, an upper portion being insertable into the bore in the distal end of the first arm, and a butt or a flange therebetween. Here the butt has a height or longitudinal extension along the direction of the shaft, and the butt has a diameter being greater than a diameter of the lower portion of the shaft, whereby the butt abuts a surface of the jaw when the lower portion is inserted into the hole or bore in the jaw.

The diameter of the butt is greater than a diameter of the upper portion of the shaft and greater than a diameter of the bore in the distal end of the first arm, whereby the level of position of the first arm in relation to the anchor member and in relation to a surface of the jaw when the lower portion is inserted into the hole or bore in the jaw is determined by the height or longitudinal extension of said butt. Thus, by using anchor members having different butt heights, various height level of the first arm in relation to the jawbone can be obtained. However, the height level of the first arm may also be varied by using the same anchor member and then using spacers of different heights, where a selected spacer may be arranged on top of the butt.

The dental handpiece may be any conventional handpiece for drilling action, said handpiece being provided with attachment means for attaching the second arm of the paralleling apparatus.

The attachment means may be any means capable of pivotably linking the handpiece to the second arm during the drilling action, said attachment means being arranged in order to secure that the drilling axis of the burr does not pass any of the arms during drilling.

In a preferred embodiment the attachment means consists of a leading pin fixed to either the handpiece or the second arm and received in a bore on the other part of the system said leading pin being arranged in parallel with the drilling action of the burr. More preferred the leading pin is fixed to the handpiece and received in a bore of the second arm. The leading pin is suitably fixed to an adapter means of the handpiece. The adapter means must be fixed to the handpiece, or even more preferred integrated with the head of the handpiece. The leading pin may be permanently fixed to the adapter means. However in order to adjust for different height levels in the jaw it is preferred that it is possible to height adjust the leading pin. Said function may be obtainable by using a fixation screw or the like for fixation of the leading pin.

In particular, the leading pin may have a rounded free end, in order to allow an easy sliding of the pin.

Many burrs are provided with a scale whereby the proceeding of the burr into the jaw may be monitored. It is however difficult to observe the scale during the drilling function. In one embodiment of the present invention, it is possible to monitor the proceeding of the burr, in that the leading pin is preferably provided with a scale such as a mm-scale. Thereby the proceeding of the leading pin in relation to the second arm and/or corresponding bush is observable as an indication of the proceeding of the burr into the jawbone.

The means for pivotably connecting the second arm to a dental handpiece comprising a burr is preferably a bore in the distal end of the second arm. More preferred the means is a bore through the arm, said bore being dimensioned to receive the leading pin on the handpiece without leaving any tolerances that would otherwise disturb the ability of securing parallel holes.

Alternatively or combined with height adjustments of the leading, in order to adjust for the various height levels in the jaw bone, a bush is preferably incorporated in the bore of the distal end of the second arm for receiving the leading pin. The bush is preferably comprising a stopping mechanism whereby the leading pin may be received in the bush until a certain stop. Thereby the handpiece may be height adjusted in relation to the anchor means, by using bushes having a stopping mechanism in different heights. Preferably a sleeve is arranged on the bush for determining the positioning level of the handpiece in relation to the second arm.

The hinging means of the invention is preferably a permanent non-releasable hinge, consisting of a bore of each arm said bore having identical dimensions for the two arms and a pin precisely driven through the two bores, whereby the two arms may rotate around an axis through the centre of the pin while any other movement is prevented. The hinging means is preferably formed so that the arms are arranged in the same horizontal plane. More preferably the first arm, the second arm and the hinging means are arranged in the same horizontal level.

Hinging means must provide a rigid connection between the two arms except of course in relation to the rotational movements, whereby no play is occurring between the arms. It is preferred that the proximal end of each arm has a contact surface with the width of said contact surface being larger than the height or thickness of the proximal end of said arm, said hinging means comprising an axle or shaft connecting the proximal ends with the two contact surfaces laying flat up to each other in a supportive way, the width being a dimension which is not parallel with the third axis of rotation. Preferably the width is substantially perpendicular to the third axis of rotation.

The hinging means providing the rotational movements of one arm in relation to the other is preferably designed to allow a movement wherein the first arm is capable of rotating in an angle in the range between 0° (arms parallely aligned) and 250° in relation to the second arm about an axis through the hinging means. These movements allow for drilling actions in most positions in the jawbones of a human being. For further improving the ability of the system to reach for all possible positions in the jawbones the paralleling apparatus is preferably constructed to be inverted whereby the first arm is being attached to the handpiece and the second arm is attached to the anchor means.

In the situation of inversion as described above it is preferred that the diameter of the bore of the first arm is identical with the diameter of the bore of the second arm. Even more preferred is an apparatus that is symmetrical about an axis parallel with the arms through the hinging means.

With respect to many applications of the system according to the invention it is advantageous to interlock the arms during the drilling action. Thus a fixation means is preferably arranged on one arm, said fixation means being provided for temporarily maintaining the angle between the first arm and the second arm during drilling. Any suitable fixation means may be used, but preferably the fixation means is a fixation screw positioned adjacent the hinging means is used.

For further adjustments, in particular for very irregular jawbones, it may be advantageous to be able to further adjust the height of the first arm in relation to the jawbone. Thus, the system of the present invention may further comprise a distance piece or distance arm having a staircase form. This distance arm may be used for insertion between the anchor member and the first arm. Here, the distance arm has a first end and a second end, with the first end adapted for being pivotably connected to the distal end of the first arm thereby defining the first axis of rotation, and with the second end adapted for being pivotably connected to the anchor member thereby defining an anchor member axis of rotation. The distance arm is formed so that the first axis of rotation is substantially parallel to the anchor member axis of rotation.

Preferably, the distance arm is formed as a two-step staircase, where an upper surface of the first end or first step of the distance arm is below a lower surface of the second end or second step of the distance arm. Thus, the distal end of the first arm is positioned at a lower level when being connected to the distance arm than when being connected directly to the anchor member. It is further preferred that the system comprises fastening or locking means for locking the position of the distance arm in relation to the anchor member.

The paralleling device may be constructed of any material which may be auto claved. The material is preferably titanium or acid-resisting steel.

In order to reduce the friction between anchor member/ leading pin and bore during attachment and releasing it is preferred that a friction reducing material is applied to other or both of the surfaces. In particular it is preferred that a teflon layer is applied to the inner surface of the bore or the other surface of the anchor member and/or the leading pin.

In the following the invention is discussed in greater detail in relation to the drawings.

Figures 1, 2, 3:
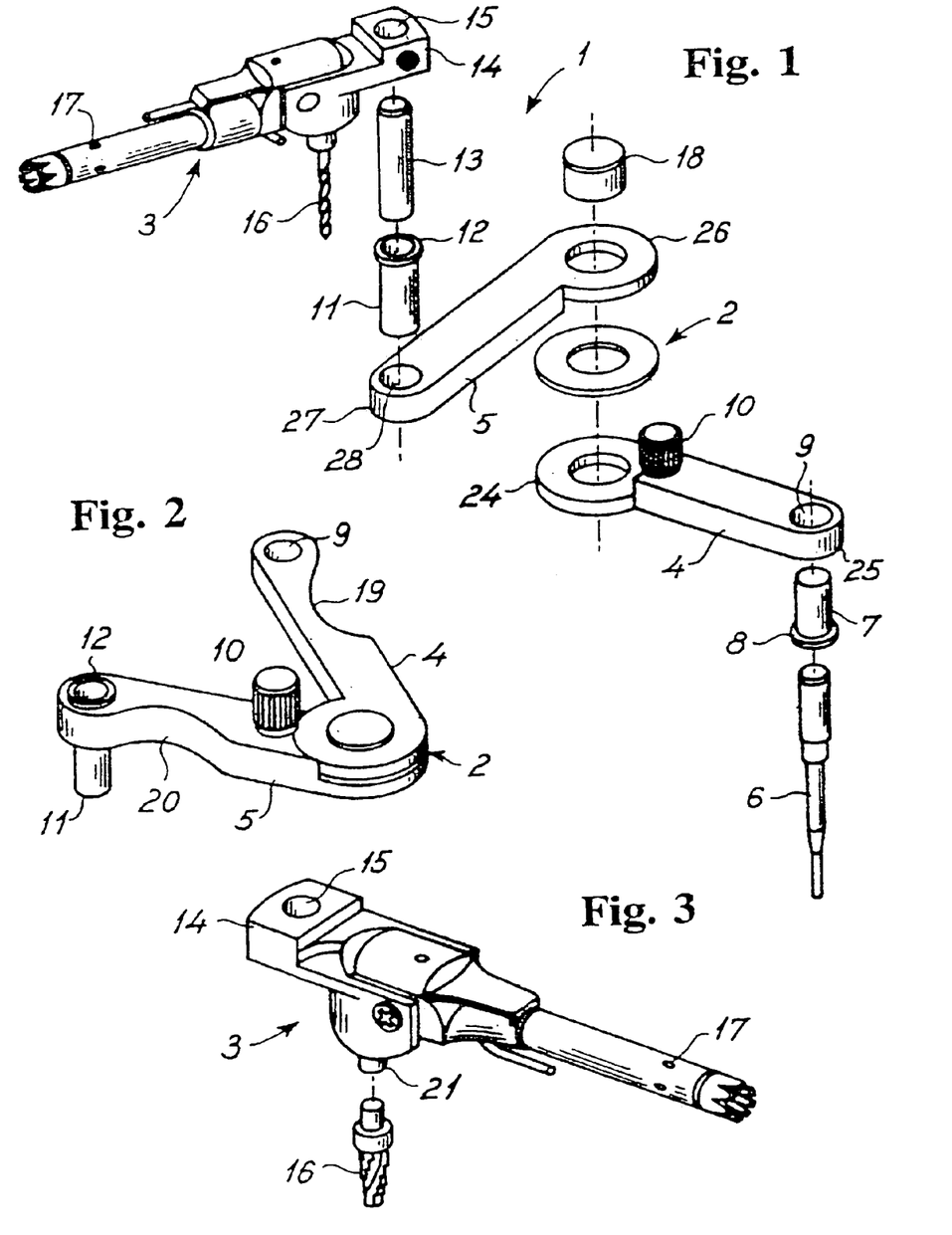
FIG. 1 is an exploded view of the system according to the invention.
FIG. 2 is an elevated side view of the paralleling apparatus according to the invention.
FIG. 3 is an elevated side view of the dental handpiece including a burr.

In FIG. 1 the system according to the invention is denoted 1 comprising a paralleling apparatus 2 and a dental handpiece 3. In FIG. 1 the paralleling apparatus 2 is consisting of a first arm 4 and a second arm 5 each having a proximal end 24, 26 and a distal end 25, 27. The arms 4 and 5 are pivotably connected through a hinging means having a pin 18. The arms 4 and 5 are pivotable around an axis through the centre of the pin 18.

In the distal end 25 of the first arm 4 a bore 9 is located as a means for pivotably connecting an anchor means 6. Said anchor means 6 may be a burr, such as a pilot burr or an anchor pin secured in the jaw, the use of which is designed as an alignment tool for drilling second holes in the jaw. Thus in use the paralleling apparatus 2 is arranged in relation to the anchor means 6 so that attachment means 9 slides over anchor means 6. It is preferred that the anchor means 6 is provided with a sleeve, in order to determine the final position of paralleling apparatus 2 in relation to the anchor means 6.

In another embodiment a bush 7 is arranged in the attachment means 9, said bush 7 then being constructed to receive the free end of the anchor means 6. The bush 7 is preferably provided with a sleeve 8 as well as a stopper mechanism so that the anchor means 6 cannot protrude further than to a predetermined level through the bore 9. The outer diameter of the bush 7 is corresponding the inner diameter of the bore 9, leading to substantially no tolerance between the attachment means 9 and the bush in the plane perpendicular to the axis of the anchor means 6. The inner diameter of the bush 7 is corresponding to the outer diameter of the anchor means 6. In particular when the anchor means 6 is a burr, such as a pilot burr, it is of importance that various bushes 7 having different inner diameter are available for receiving various burrs.

Figure 7:
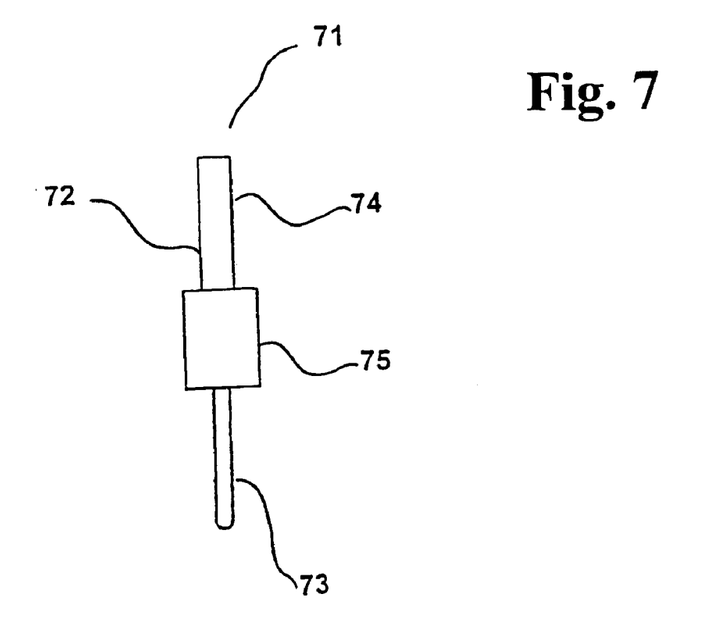
FIG. 7 shows an anchor member according to the invention.

Another embodiment of an anchor member according to the invention is shown in FIG. 7. Here the anchor member 71 has a shaft 72 which consists of a lower portion 73, an upper portion 74 and a butt 75. The diameter of the butt 75 is greater than the diameter of the lower portion 73, the diameter of the upper portion 74, and the diameter of the bore 9 in the distal end 25 of the first arm 4. When the lower portion 73 of the anchor member 71 inserted in the hole in the jaw, the butt 75 rests on the surface of the jaw, and when the first arm 4 is arranged on the anchor member 75 by having the upper portion 74 inserted into the bore 9, the position level or height of the firsts arm may be determined by the height of the butt 75. By using anchor members with different butt heights, the position level of the first arm may be varied.

Turning back to FIG. 1, in the distal end 27 of the arm 5 a bore 28 is located as the attachment means for pivotably attaching a leading pin 13 of the adapter means 14 of the dental handpiece 3. The leading pin 13 is designed to fit slidingly in the bore 28. In preferred embodiment a bush 11 is arranged in the bore 28 for receiving the leading pin 13. The bush 11 is preferably provided with a sleeve 12 for determining an end position of the bush 11. The bush 11 may be an open-ended bush whereby the leading pin 13 is capable of sliding through the bush 11. In another embodiment the bush 11 is provided with a stopping mechanism so that the leading pin 13 is forced to stop at a predetermined point when entered into the bush 11. By using bushes of the latter type in combination with corresponding bushes for the anchor means it is possible to correct for the different heights in the jawbone and thereby determine the precise depth of the hole to be drilled.

As may be seen from FIG. 1 the burr 16 does not pass through any of the arms 4 and 5 during the drilling function, thus the drilling axis of the burr is at a distance to the second arm.

A fixation screw 10 is located adjacent the hinging means for locking the arm 4, 5 in a predetermined angle in relation to each other. The fixation screw 10 may be activated before the paralleling apparatus 2 is arranged in situ, this being particularly relevant if the drilling action is performed on a model prior to being performed in situ. Alternatively, the fixation screw 10 may be activated after the paralleling apparatus 2 has been arranged in situ prior to the drilling action.

In FIG. 2 each of the arms 4, 5 of the paralleling apparatus 2 are provided with a recess 19, 20 providing a greater range of movement of the burr while at the same time providing a lighter instrument.

FIG. 3 shows a dental handpiece 3 according to the invention. The handpiece 3 is provided with a means 17 for connection to a rotating energy source, a burr attachment means 21 for releasably receiving the burr and an adapter means 14 for attaching the paralleling apparatus 2. In FIG. 3 the adapter means 14 is an integrated part of the head of the dental handpiece whereby the risk of tolerances at this point is eliminated. The adapter means 14 is provided with a bore 15 for receiving the leading pin 13. During the drilling function the leading pin 13 is fixed in the bore 15. In one embodiment of the invention it is possible to adjust the position of the leading pin 13 prior to drilling, it is however often preferred that the leading pin 13 is permanently fixed and any height adjustments are carried out by use of various bushes 11.

Figure 4A:
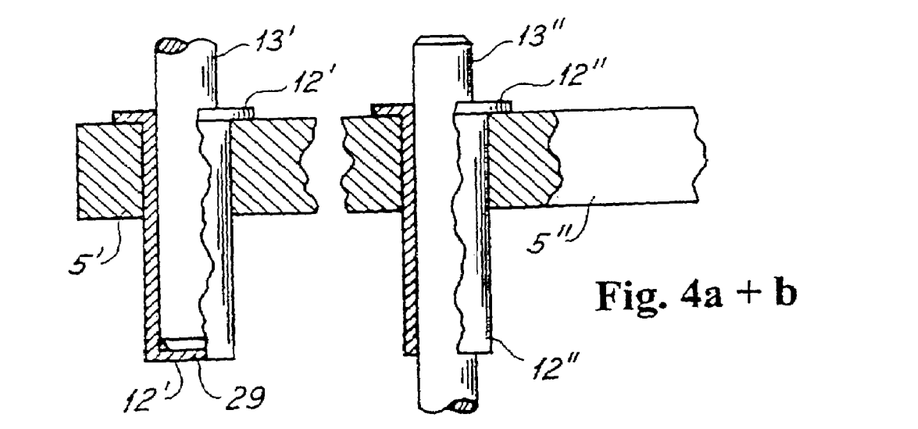

FIG. 4 a shows a partially cross-section view of a bush, such as a bush 12' for receiving the leading pin 13'. The bush 12' is provided with a stopping mechanism 29 serving as a stopping mechanism for the leading pin 13' in order to predetermine the drilling depth possible. The bush 13' is furthermore provided with a sleeve 12'. FIG. 4b shows a partially cross-section view of a bush, such as a bush 12" for receiving the leading pin 13". The bush 12' is not provided with a stopping mechanism whereby the leading pin 13" may be entered through the bush 13". The bush 13' is furthermore provided with a sleeve 12".

Figure 5:
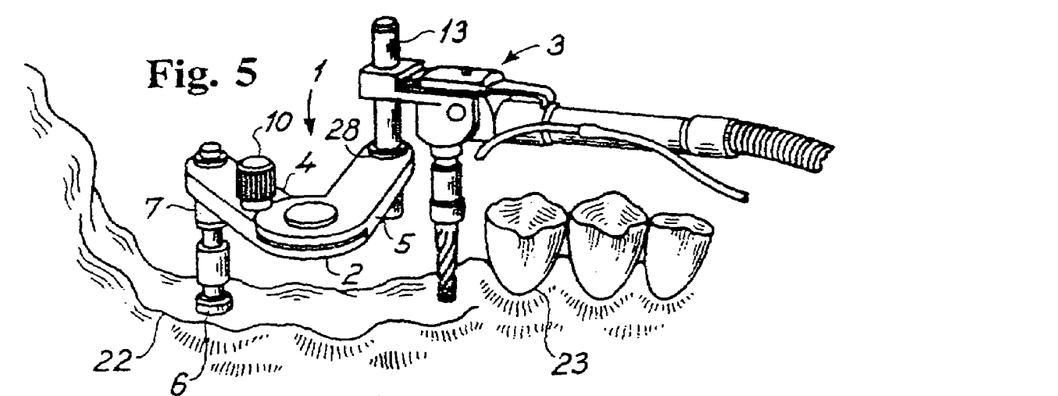
FIG. 5 shows the system according to the invention during drilling a hole in the jaw.
Figure 6:
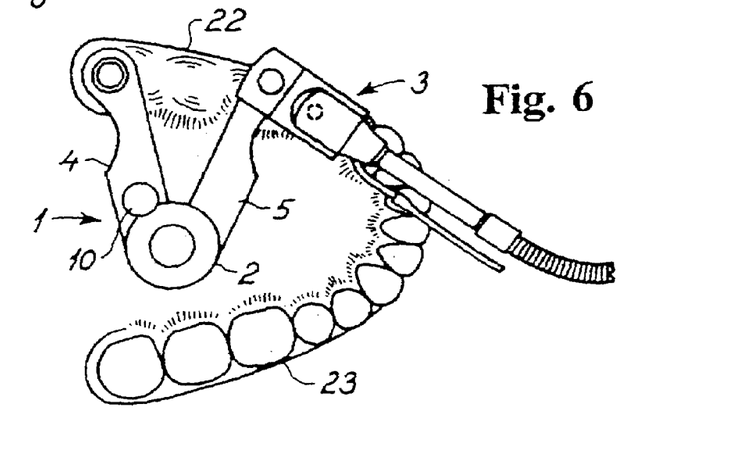
FIG. 6 is a plane view of the system of FIG. 5.

In FIG. 5 and FIG. 6 the system 1 according to the invention is arranged in situ for drilling a second hole in the jaw bone 22 adjacent the existing teeth 23 of the jaw. A first hole has been drilled in the jawbone, a so-called pilot hole, wherein the anchor means 6 is arranged. Then the paralleling apparatus 2 is arranged by sliding arm 4 including a bush 7 over the free end of the anchor means 6 situated in the jaw bone. After having decided the required angle between the arms 4, 5 the fixation screw 10 is activated to interlock the two arms 4, 5. Thereafter the dental handpiece 3 is positioned with the leading pin 13 into the bore 28. The final adjustments before drilling are carried out by rotating the paralleling apparatus 2 about an axis through the centre of the anchor means 6 and rotating the dental handpiece 3 about an axis through the leading pin 13. The longitudinal axis of the hole drilled is parallel with the longitudinal axis through the anchor means. The next hole to be drilled may be performed by simply releasing the fixation screw, rotating the paralleling apparatus 2 into a new position, interlocking the two arms 4,5 and perform the drilling action.

In case the position of the next hole is not reachable by rotating arm 5 in relation to arm 4, it is possible to invert the paralleling apparatus 2 as discussed above. Thereby another range is reachable for drilling the necessary hole for the implant.

Figure 8:
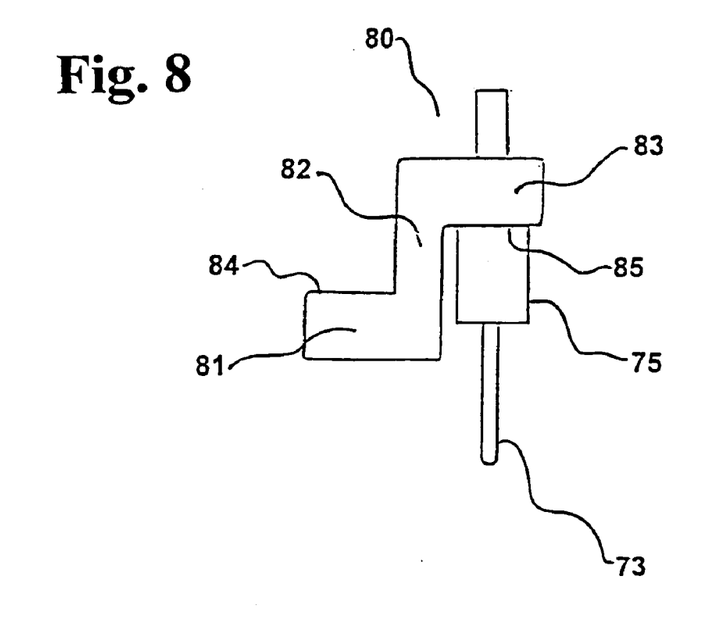
FIG. 8 shows staircase formed distance piece according to the invention.

In some cases a further distance piece or arm may be used. In FIG. 8 is shown a distance piece or distance arm formed as a two-step staircase. The distance arm 80 has a first end or first step 81, a connecting part 82 and a second end or second step 83. Here the upper surface 84 of the first step 81 is positioned below the lower surface 85 of the second step 83. The attachment means 9 of the first arm 25 can be pivotably connected to the first step 81, where pivot means corresponding to the upper part of the anchor means 6 inserted in the jaw may be provided. The second step 83 is provided with a bore for being pivotably connected to anchor means 6 inserted in the jaw. Furthermore locking means may be provided for securing the second step 83 to the anchor means 6 in the jaw.

The invention further relates to a method for parallel insertion of a dental implant in a jawbone comprising establishing a first hole in the jawbone,
  arranging an anchor means in the hole,
  using said anchor means as a pivot guide for an arm of a system as defined above,
  guiding a handpiece attached to the system said handpiece comprising a burr for drilling second hole(s) in the jaw bone that are parallel with the first hole, and
  inserting the implant.

In the present context the jawbone is intended to include jawbone as such, a tooth root and/or an existing tooth. Also the method is useful for providing holes in the jawbone being parallel with attachments on existing teeth. In the latter the anchor member may be inserted in the attachment.

The handpiece may be provided with a direction indicated, in particular as a guidance for the dentist when making the first hole, i.e. before the parallelling device is introduced.

Before carrying out the method positioning of the apparatus may be examined in a model of the jaw. In this case it is advantageous to fix the arms of the system in relation to each other in a predetermined angle prior to the system being attached to the anchor means, because the predetermined angle may be determined in the jaw model.

When the height level of the second hole differs from that of the first hole a bush for receiving the anchor means is preferably arranged in the first arm, and a bush for receiving a leading pin of the handpiece is preferably arranged in the second arm, said bushes bearing sleeved in different levels providing for drilling the second hole in another height than the first hole.

During the drilling function it is preferred that the burr is cooled. In normal dental practice the burrs a preferably water cooled during drilling. Due to the arrangement of the burr, whereby the drilling axis does not pass any of the arms it is possible to water cool the burr during drilling. As a further advantage of the present invention it is possible to observe the burr during the drilling function. Thereby the function may be monitored in particular with respect to the actual water cooling and/or the proceeding of the burr and the appearance of jaw chips.

Yet an advantage of the present invention is the ability of inserting the implants themselves by use of the system. Some implants are to be inserted by means of a drilling means, such as the dental handpiece, and these implants are mostly provided with a mandrill fitting into the burr securing means of the dental handpiece. Accordingly, in one embodiment the invention relates to a method wherein the insert is inserted by arranging the mandrill in the securing means of the dental handpiece attaching the handpiece to the paralleling system and rotating the implant into the second hole in the jaw. In case the implant does not require a pre-drilled hole, it is also possible to use the present system for inserting the implant, by replacing the step of drilling the second hole with a step of rotating the implant into the jaw. The implants may be any implants used for providing anchor points in the jaw to which supports are made for a single tooth, several teeth, bridges and/or prosthetic devices, such as partially or total prosthetic devices.

A further object of the present invention is the use of the system described above for drilling implant holes for inserting dental implants. Since the system may be used with burrs of any diameters the system may be used for inserting a wide variety of implants. Thus, the system may be used to insert implants of any fabricate, such as ITI, Brånemark, Astra, 3i, and Frialith.

What is claimed is:

1. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way; and wherein at least one of the proximal ends of said arms comprises a bore for receiving said axle or shaft, and wherein the diameter of said bore is larger than the height of the bore.

2. An apparatus according to claim 1, wherein the hinging means and/or at least one arm comprise fixation means for locking two pivotably connected arms at a fixed angle.

3. An apparatus according to claim 1, wherein the first arm comprises means for determining the level of position of the first arm in relation to the anchor member.

4. An apparatus according to claim 1, wherein the second arm comprises means for determining the level of position of the handpiece in relation to the second arm.

5. An apparatus according to claim 1, wherein at least two of said arms are non-releasably connected.

6. An apparatus according to claim 1, wherein the first and/or second arm comprises means for determining the level of position of the second arm in relation to the first arm.

7. An apparatus according to claim 1, wherein the first arm, the second arm and hinging means are arranged substantially in the same horizontal level.

8. An apparatus according to claim 1, wherein the means for pivotably connecting the anchor member is a bore in the distal end for the first arm.

9. An apparatus according to claim 8, wherein a bush is incorporated in the bore of the distal end of the first arm for receiving the anchor member.

10. An apparatus according to claim 9, wherein a collar is arranged on the bush for determining the level of position of the first arm in relation to the anchor member.

11. An apparatus according to claim 1, wherein the means for pivotably connecting attachment means of the dental handpiece comprises a bore in the distal end of the second arm.

12. An apparatus according to claim 11, wherein a bush in incorporated in the bore of the distal end of the second arm.

13. An apparatus according to claim 1, wherein the third axis of rotation is substantially parallel to the first and second axes of rotation.

14. An apparatus according to claim 1, wherein a third arm is pivotably connected by hinging means to the first or the second arm thereby defining the third axis of rotation and a fourth axis of rotation.

15. An apparatus according to claim 1, wherein the apparatus further comprises a staircase formed distance piece or distance arm, said distance arm having a first end and a second end, with the first end being adapted for being pivotably connected to the distal end of the first arm thereby defining the first axis of rotation, and with the second end being adapted for being pivotably connected to the anchor member thereby defining an anchor member axis of rotation, said first axis of rotation being substantially parallel to the anchor member axis of rotation.

16. An apparatus according to claim 1, wherein the first arm is capable of rotating at an angle selected from the interval of 0° to 250° in relation to said second arm about an axis through the hinging means.

17. An apparatus according to claim 1, wherein each arm contains a bore and the diameter of the bore of the first arm is substantially identical with the diameter of the bore of the second arm.

18. A method for parallel insertion of a dental implant in a jaw bone comprising
establishing a first hole in the jaw bone,
arranging an anchor means in the hole,
using said anchor means as a pivot guide for an arm of a system or an apparatus as defined in claim 1
guiding a handpiece attached to the system, said handpiece comprising a burr for drilling second hole(s) in the jaw bone that are parallel with the first hole, and inserting the implant.

19. A method according to claim 18, wherein the arms of the system are fixed in relation to each other in a predetermined angle prior to the system being attached to the anchor means.

20. A method according to claim 18, wherein a bush for receiving the anchor means is arranged in the first arm, and a bush for receiving a leading pin of the handpiece is arranged in the second arm, said bushes bearing collars in different levels providing for drilling the second hole in another height levels than the first hole.

21. A method according to claim 18, wherein the burr is cooled during drilling.

22. A method according to claim 21, wherein the burr is water cooled.

23. A method according to claim 18, wherein the implant comprises a mandrill for inserting in a burr securing means of the dental handpiece.

24. A method according to claim 23, wherein the implant is inserted by arranging the mandrill in the securing means of the dental handpiece attaching the handpiece to the paralleling system and rotating the implant into the second hole in the jaw.

25. An Apparatus according to claim 1, further including a spacer between the proximal ends of both arms.

26. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein the hinging means and/or at least one arm comprise fixation means for locking two pivotably connected arms at a fixed angle.

27. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein the first arm comprises means for determining the level of position of the first arm in relation to the anchor member.

28. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein the second arm comprises means for determining the level of position of the handpiece in relation to the second arm.

29. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein at least two of said arms are non-releasably connected.

30. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein the first and/or second arm comprises means for determining the level of position of the second arm in relation to the first arm.

31. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein the first arm, the second arm and hinging means are arranged substantially in the same horizontal level.

32. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein the means for pivotably connecting attachment means of the dental handpiece comprises a bore in the distal end of the second arm.

33. An apparatus or paralleling device for parallel insertion of dental implants, said apparatus comprising: at least a first arm and a second arm, said arms having a proximal end and a distal end, said first arm comprising means for pivotably connecting an anchor member thereby defining a first axis of rotation, said second arm comprising means for pivotably connecting attachment means of a dental handpiece thereby defining a second axis of rotation, said proximal ends of the first and second arms being pivotably connected by hinging means defining a third axis of rotation, and for the first and second arms, the proximal end of an arm has a contact surface with the width of said contact surface being larger than the height of thickness of the proximal end of the arm, said hinging means comprising an axle or shaft connecting the proximal ends with the two contact surfaces laying flat up to each other in a supportive way, and wherein the apparatus further comprises a staircase formed distance piece or distance arm, said distance arm having a first end and a second end, with the first end being adapted for being pivotably connected to the distal end of the first arm thereby defining the first axis of rotation, and with the second end being adapted for being pivotably connected to the anchor member thereby defining an anchor member axis of rotation, said first axis of rotation being substantially parallel to the anchor member axis of rotation.

* * * * *